US008685684B2

(12) United States Patent
Lee et al.

(10) Patent No.: US 8,685,684 B2
(45) Date of Patent: Apr. 1, 2014

(54) PROCESS FOR THE PRODUCTION OF BIO-FUELS AND/OR BIO-CHEMICALS FROM BIOMASS FERMENTATION

(75) Inventors: Julia Lee, Gyeonggi-do (KR); Hyo Hak Song, Daejeon (KR); Moon Ho Ueom, Daejeon (KR); Jung Hee Cho, Daejeon (KR); Do Young Seung, Seoul (KR); Gi-Wook Choi, Jeonbuk (KR); Se-Kwon Moon, Jeonbuk (KR); Sung Hoon Park, Busan (KR); Yule Kim, Jeonbuk (KR); Min Hee Han, Jeonbuk (KR)

(73) Assignees: GS Caltex Corporation, Seoul (KR); Changhae Ethanol Co., Ltd., Jeonbuk (KR)

( * ) Notice: Subject to any disclaimer, the term of this patent is extended or adjusted under 35 U.S.C. 154(b) by 0 days.

(21) Appl. No.: 13/396,000

(22) PCT Filed: Sep. 13, 2010

(86) PCT No.: PCT/KR2010/006199
§ 371 (c)(1),
(2), (4) Date: May 31, 2012

(87) PCT Pub. No.: WO2011/031104
PCT Pub. Date: Mar. 17, 2011

(65) Prior Publication Data
US 2012/0231511 A1 Sep. 13, 2012

(30) Foreign Application Priority Data
Sep. 14, 2009 (KR) .......................... 10-2009-0086543
Aug. 25, 2010 (KR) .......................... 10-2010-0082562

(51) Int. Cl.
*C12P 7/08* (2006.01)

(52) U.S. Cl.
USPC .......................................................... 435/163

(58) Field of Classification Search
USPC .......................................................... 435/163
See application file for complete search history.

(56) References Cited

U.S. PATENT DOCUMENTS

| 4,578,353 | A | 3/1986 | Assarsson et al. |
| 2002/0164731 | A1 | 11/2002 | Eroma et al. |
| 2004/0084366 | A1 | 5/2004 | Anderson et al. |
| 2007/0031919 | A1 | 2/2007 | Dunson et al. |
| 2007/0178569 | A1 | 8/2007 | Leschine et al. |
| 2008/0003654 | A1* | 1/2008 | Hirl ................. 435/162 |
| 2008/0193989 | A1 | 8/2008 | Verser et al. |
| 2009/0081747 | A1 | 3/2009 | Pearson |

FOREIGN PATENT DOCUMENTS

| JP | 2010-510800 A | 4/2010 |
| KR | 10-2010-0064756 | 6/2010 |
| WO | WO-2008/115080 A1 | 9/2008 |

OTHER PUBLICATIONS

Park, Bio-Refinery: Production of Fuels, Chemicals, and Polymers Using Biological Resources, News & Information for Chemical Engineering, 26(1): 48-56 (2008) (English abstract included).
International Search Report for PCT/KR2010/006199 dated May 20, 2011.
Aeschlimann et al., The Effect of Yeast Extract Supplementation on the Production of Lactic Acid from Whey Permeate by *Lactobacillus helveticus*, Appl. Microbiol. Biotechnol., 32:398-402 (1990).
Akhtar et al., Corn Steep Liquore Lowers the Amount of Inoculum for Biopulping, Tappi Journal, 80(6):161-154 (1997).
Amartey et al., Bulletin of Chemists and Technologists of Macedonia, 19(1): 65 (2000).
Atkinson et al., Biochemical Engineering and Biotechnology Handbook, The Nature Press, NY, 57 (1983).
Bafrncova et al., Improvement of Very High Gravity Ethanol Fermentation by Media Supplementation using *Saccharomyces cerevisiae*, Biotechnology Letter, 21:337-341 (1999).
Bibal et al., Enhanced Inhibitory Effect of Lactic Acid on Growth Kinetics of *Streptococcus cremoris* During Nutritional Medium Limitations, Applied Mircobiology Biotechnology, 30:630-635 (1989).
Bury et al., Effect of Yeast Extract Supplementation of β-Galactosidase Activity of *Lactobacillus delbrueckii* subsp. Bulgaricus 11842 Grown in Whey, Czech J. Food Sci., 19:166-170 (2001).
Kazamias et al., Enhanced Fermentation of Mannitol and Release of Cytotoxin by *Clostridium difficile* in Alkine Culture Media, Applied and Environmental Microbiology, 61(6):2425-2427 (1995).
Laube et al., The Effect of Yeast Extract on the Fermentation of Glucose to 2, 3-Butanediol by *Bacillus polymyxa*+Biotechnol. Lett., 6:535-540 (1984).
Liggett et al., Corn Steep Liquor in Microbiology, Bacteriol. Rev., 12:297-299 (1948).
Liggett et al., Corn Steep Liquor in Microbiology, Bacteriol. Rev., 12:300-311 (1948).
Miller et al., Manual of Industrial Microbiology and Biotechnology, American Society of Microbiology, Washington DC, 122 (1986).

(Continued)

*Primary Examiner* — Ralph Gitomer
(74) *Attorney, Agent, or Firm* — The PL Law Group, PLLC

(57) ABSTRACT

Disclosed is a preparation method for bio-fuel materials and bio-chemicals comprising the following steps: preparing a medium comprising fermentation waste generated in an alcohol production process; inoculating a first microorganism into the medium; and culturing the medium wherein the first microorganism was inoculated. More specifically, the preparation method for bio-fuel materials and bio-chemicals comprises the following steps: fermenting hexoses from a mixture of pentoses and hexoses to produce an ethanol fermentation broth; separating and purifying the ethanol fermentation broth; preparing a medium comprising the fermentation waste produced in the separation and purification step; inoculating a first microorganism into the medium; and culturing the medium wherein the first microorganism was inoculated.

13 Claims, 13 Drawing Sheets

(56) References Cited

OTHER PUBLICATIONS

Mulligan et al., Continuous Production of Ammonium Lactate by *Streptococcus cremoris* in a Three-Stage Reactor, Biotechnology and Bioengineering, 38:1173-1181 (1991).

Norton et al., Reduction of Yeast Extract Supplementation in Lactic Acid Fermentation of Whey Permeate by Immobilized Cell Technology, J. Dairy Sci., 77:2494-2508 (1994).

Ojokoh et al., Production of *Saccharomyces cerevisiae* Biomass in Papaya Extract Medium, African Journal of Biotechnology, 4(11):1281-1284 (2005).

Potvin et al., An Automatic Turbidimetric Method to Screen yeast Extracts as Fermentation Nutrient Ingredients, Journal of Microbiological Methods, 29:153-160 (1997).

Revillion et al., Production of Yeast Extract from Whey using *Kluyveromyces marxianus*, Brazilian Archives of Biology and Technology, 46(1):121-127 (2003).

Silveira et al., Production of Glucose-Fructose Oxidoreductase and Ethanol by *Zymomonas mobilis* ATCC 29191 n Medium Contatining Corn Steep Liquor as a Source of Vitamins, Appl. Microbiol. Biotechnol., 55:442-445 (2001).

Underwood et al., Lack of protective Osmolytes Limits Final Cell Density and Volumetric Productivity of Ethanologenic *Escherichia coli* KO11 during Xylose Fermentation, Applied and Environmental Microbiology, 70:2734-2740 (2004).

Zhang et al., Chemically Defined Media for Commercial Fermetations, App. Microbiol. Biotechnol., 51:407-421 (1997).

\* cited by examiner

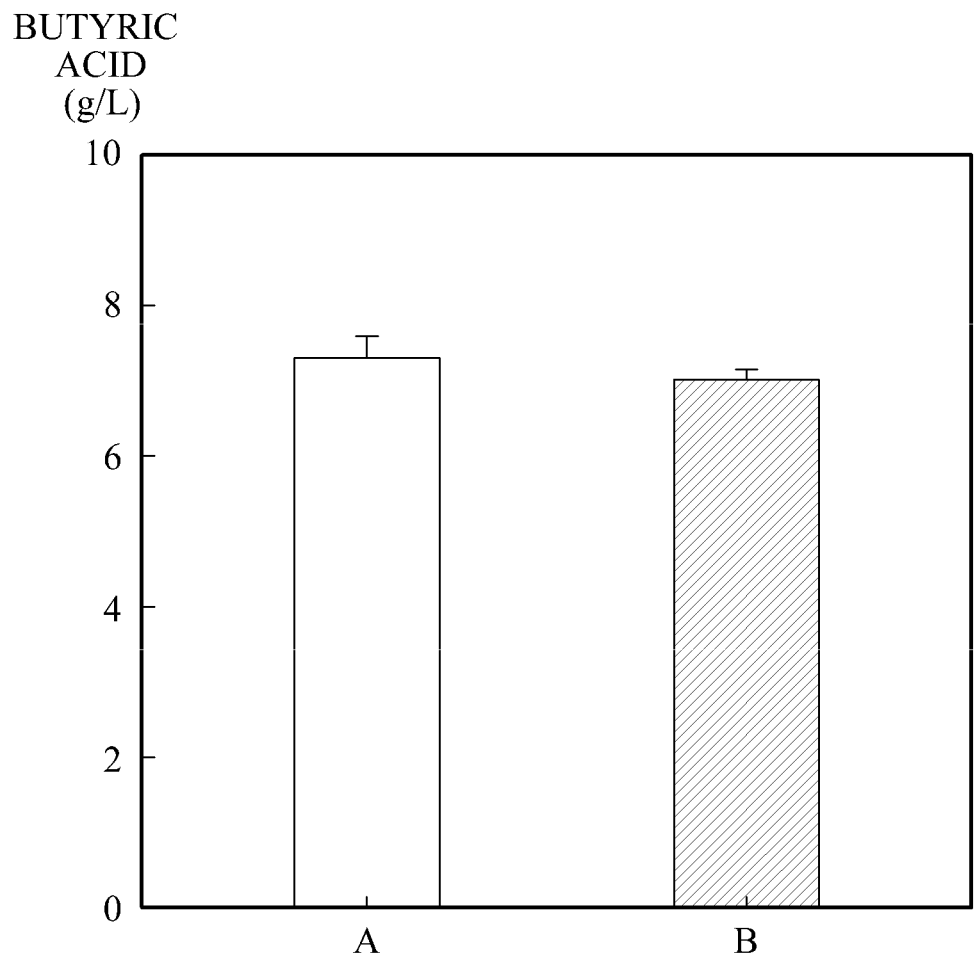

PROCESS FOR THE PRODUCTION OF BIO-FUELS AND/OR BIO-CHEMICALS FROM BIOMASS FERMENTATION

CROSS-REFERENCE TO RELATED APPLICATIONS

This application is a National Phase application under 35 U.S.C. §371 of International Application No. PCT/KR2010/006199, filed Sep. 13, 2010 and published as WO 2011/031104 on Mar. 17, 2011, which claims priority to Korean patent application serial numbers KR 10-2009-0086543, filed Sep. 14, 2009, and KR 10-2010-0082562, filed Aug. 25, 2010, the entirety of each of which is hereby incorporated herein by reference.

TECHNICAL FIELD

The present invention relates to a method for preparing biofuels and biochemicals, and more particularly, to a method for preparing economical and environmentally friendly biofuels and biochemicals that may remarkably reduce the cost of feedstock and energy involved in the preparation process.

BACKGROUND ART

Artificially culturing microorganisms in a specific environment requires various nutrient components to be added to a culture medium, and the required nutrient components vary depending on the types of microorganisms to be cultured. To meet the nutrient requirements, generally various culture media containing nutrient components of minerals, amino acids, vitamins, peptones, corn steep liquor, yeast extract, and the like have been developed and used. A culture medium for microorganisms is largely classified into a synthetic medium only containing chemically defined nutrient components such as minerals, amino acids, vitamins, and the like, and a complex medium containing chemically undefined nutrient components such as peptones, corn steep liquor, yeast extract, and the like.

To develop a synthetic medium, identification of all the nutrient components by a corresponding type of microorganism is required, since required nutrient components vary depending on the types of microorganisms as described above. Generally, in order to identify all the required nutrient components, all amino acids and vitamins are added to a culture medium containing minerals, so as to culture a given microorganism on the culture medium, and to check whether the microorganism grows. When growth of the microorganism is observed, after preparing a fresh culture medium by removing one of the nutrient components added to the culture medium, the microorganism is cultured on the culture medium from which a specific nutrient component is removed, and then, a check is performed to determine whether the microorganism grows. When growth of the microorganism is observed, another fresh culture medium is prepared by removing another nutrient component from among the nutrient components added to the initial culture medium. Conversely, when growth of the microorganism is not observed, the removed nutrient component is determined to be an essential nutrient component that is to be added during preparation of a synthetic medium, and afterwards, is necessarily added when preparing a culture medium. Recently, a synthetic medium has been developed by repeatedly performing this method of identifying all the nutrient components necessary for microorganism cultivation (Zhang et al., App. Microbiol. Biotechnol., 51:407, 1997). However, since this method is based on a single omission technique involving repeated trial and error, it requires a great deal of time, human effort, and is not cost effective. To compensate for the shortcomings of the single omission technique, several statistical techniques have been recently suggested for developing a culture medium, but are not widely used due to a low probability of success associated with these statistical techniques.

After identifying all the nutrient components necessary for microorganism cultivation using a single omission technique or a statistical technique, determination of an optimum amount of each nutrient component to be added to the culture medium, necessary to promote the microorganism growth, is required. This also requires a great deal of time, human efforts, and is not cost effective. In particular, a disadvantage in that a considerable number of microorganisms disadvantageously cannot grow in a synthetic medium containing all amino acids and vitamins has been reported, and a majority of microorganisms grow better in a culture medium containing peptones or yeast extract added, as a nutrient component, to a complex medium rather than a synthetic medium. First of all, since chemically defined nutrient components added to a synthetic medium such as amino acid or vitamin are costly, a limitation exists in using a synthetic medium containing such expensive nutrient components in the production of biofuels and biochemicals on an industrial scale through microorganism cultivation.

In the production of biofuels and biochemicals through microorganism cultivation, a complex medium containing peptones, corn steep liquor, or yeast extract that includes most of all the nutrient components necessary for microorganism cultivation, although the nutrient components are chemically undefined, is being widely used. A peptone is a product obtained in the hydrolysis of protein, and when converted to amino acid by peptidase, can be used as a carbon source in the cultivation of microorganism. However, use of peptones to produce biofuels and biochemicals on an industrial scale, through microorganism cultivation, is too expensive. Corn steep liquor is a by-product derived from corn wet milling, and due to a very low cost, has been widely used as an important nutrient component of a culture medium for microorganism (Liggett et al., Bacteriol. Rev., 12:297, 1948; Liggett et al., Bacteriol. Rev., 12:300, 1948). Also, corn steep liquor is a good carbon source for microorganism cultivation and has an advantage of including other various nutrient components, as well as vitamins and amino acids (Atkinson et al., *Biochemical Engineering and Biotechnology Handbook*, The Nature Press, NY, 57, 1983; Miller et al., *Manual of Industrial Microbiology and Biotechnology*, American Society of Microbiology, Washington, D.C., 122, 1986; Akhtar et al., Tapi J. 80:161, 1997). Although corn steep liquor is a suitable, low cost, nutrient component in the cultivation of microorganisms corn steep liquor has a disadvantage of having to be added to a culture medium in larger amounts, when compared to peptones or yeast extract. Also, since corn steep liquor includes an unknown component that inhibits microorganism growth, when compared to the same amount of yeast extract, corn steep liquor is inferior in terms of microorganism growth rate, concentration of microorganisms, and productivity of a target substance (Amartey et al., *Bullet. Chem. Technol.*, Macedonia, 19:65, 2000; Silveira et al., Appl. Microbiol. Biotechnol., 55:442, 2001; Underwood et al., Appl. Environ. Microbiol., 70:2734).

Yeast extract is proved as a superior nutrient component for microorganism cultivation by many researchers, and in particular, yeast extract has been reported to improve the productivity of a target substance through microorganism cultivation by promoting microorganism growth (Laube et al., Biotechnol. Lett., 6:535, 1984; Bibal et al., Appl. Microbiol. Biotechnol., 30:630, 1989; Aeschlimann et al., *Appl. Microbiol. Biotechnol.,* 32:398, 1990; Norton et al., *J. Dairy Sci.,* 77:2494, 1994; Kazamias et al., *Appl. Environ. Microbiol.,* 61:2425, 1995; Potvin et al., *J. Microbiol. Methods,* 29:153, 1997; Bafrncova et al., *Biotechnol. Lett.,* 21:337, 1999; Bury et al., *Czech J. Food Sci.,* 19:166, 2001). Also, since yeast extract includes a considerable amount of carbohydrates and soluble sugars, yeast extract provides both a nutrient component and a carbon source in the cultivation of microorganisms (Revillion et al., *Braz. Arch. Biol. Technol.,* 46:121, 2003; Ojokoh et al., *Afr. J. Biotechnol.,* 4:1281, 2005). Due to this superior characteristic, yeast extract is being widely used as an additive in the food industry. Generally, yeast extract is made by artificially growing a strain of *Saccharomyces cerevisiae* that is a species of yeast used in production of beer and bread, followed by autolysis. However, as a matter of fact, yeast extract made through this process is improper as a nutrient component of a culture medium for producing biofuels and biochemicals on an industrial scale because of a very high cost. When producing lactic acid using substantially 2 g/L of yeast extract as a nutrient component, it is reported that the cost of the yeast extract corresponds to 32% of the total production cost of the lactic acid (Mulligan et al., *Biotechnol. Bioeng.,* 38:1173, 1991).

Studies on the production of biofuels and biochemicals through microorganism cultivation are directed to the development of low-priced carbon sources and culture mediums, development of a fermentation process, development of a separation and purification process, and development of a superior strain. Currently, when producing biofuels and biochemicals on an industrial scale through microorganism cultivation, a complex medium containing corn steep liquor, yeast extract, and peptones as major nutrient components is being widely used. As described in the foregoing, corn steep liquor has a low cost but cannot guarantee productivity of a target substance since it inhibits microorganism growth. Yeast extract and peptones are superior nutrient components but cannot guarantee economical efficiency since they are costly. Accordingly, there is an urgent demand for development of a culture medium, of low cost, that sufficiently contains superior nutrient components and can guarantee productivity and economical efficiency in production of biofuels and biochemicals on an industrial scale.

Some studies have been conducted on recycling a by-product produced in the microorganism fermentation. For example, U.S. Pat. No. 4,578,353 discloses a process in which a non-fermented solid carbohydrate residue generated in the alcohol fermentation is hydrolyzed in a sludge tank again and the hydrolysate is re-supplied as a carbon source to the same alcohol fermentation tank. WO 2008/115080 discloses a process in which two alcohol fermentation tanks are linked and an organic acid and a gaseous component produced as a by-product in each fermentation tank are selectively separated and recycled. However, these arts are limited in that they selectively recycle only some components of a material provided as a feedstock or a substance produced as a by-product in a fermentation tank by microorganisms.

Unlike fuels and chemicals produced using fossil resources as a feedstock, biofuels and biochemicals can be obtained using, as a feedstock, biomass that is a biological resource enabling complete circulation of resources. Recently, in an effort to overcome the energy crisis brought about by exhaustion of fossil fuels and environmental crises such as a climatic change caused by a build-up of greenhouse gases in the atmosphere, demand is increasing for carbon-neutral or carbon-zero and environmentally friendly biofuels and biochemicals that enable the complete circulation of resources and carbon dioxide. In particular, since delivery and storage of liquid biofuels such as, ethanol and butanol, is easy and thus, suitable for use as transportation fuels, liquid biofuels are gaining attention.

To date, biofuels and biochemicals have been primarily produced through microorganism fermentation of glucose obtained by hydrolyzing corn starch or wheat, or sucrose included in sugar cane. However, as crop costs continue to increase and use of food resources in production of biofuels and biochemicals is being raised as a moral issue, attempts have been actively made, on a global scale, to efficiently produce biofuels and biochemicals by using, as a feedstock, lignocellulosic biomass since it is an abundant non-food biological resource that is readily available across the world.

Lignocellulosic biomass may be largely divided into a woody biomass and a grassy biomass, and contains cellulose, hemicellulose, and lignin as major components.

After lignocellulosic biomass is removed through physical and chemical pre-processing using an acid, a base, or a vapor, the pre-processed lignocellulosic biomass is hydrolyzed by a hydrolase so that cellulose is converted to hexose including glucose, and hemicellulose is converted to pentose including xylose and arabinose, as well as hexose. It is known that most microorganisms are capable of utilizing hexose, in particular, glucose as a carbon source and an energy source during fermentation, however, some microorganisms are incapable of utilizing pentose as a carbon source and an energy source.

Accordingly, when producing biofuels and biochemicals through fermentation of a microorganism either incapability of or having a remarkably low capability of utilizing pentose, it is impossible to use pentose that is about 35% of the total sugar derived from lignocellulosic biomass. As a result, a subsequent increase of the feedstock cost would make it difficult to ensure the economical efficiency. Also, due to pentose being present in the wastewater produced after fermentation leading to a rapid increase in the chemical oxygen demand and biological oxygen demand, a separate process for treating the wastewater is required.

Accordingly, there is a need for development of a method for preparing biofuels and biochemicals in an economical and environmentally friendly manner while making efficient use of pentose and hexose derived from lignocellulosic biomass.

DISCLOSURE OF INVENTION

Technical Goals

An aspect of the present invention provides a method for preparing environmentally friendly and economical biofuels and biochemicals that may remarkably reduce costs of feedstock, a culture medium, and energy involved in the preparation process.

Technical Solutions

According to an aspect of the present invention, there is provided a method for preparing biofuels including preparing a culture medium containing a fermentation waste generated in alcohol production, inoculating a first microorganism into the culture medium, and culturing the first microorganism on the culture medium. The fermentation waste may be a fermentation waste with or without solids. The method for preparing biofuels may include preparing a culture medium containing a fermentation waste generated in the alcohol production or a waste produced by autolysis of the fermentation waste, and adding at least one selected from the group consisting of water, a carbon source and a nutrient component to the prepared culture medium, before inoculating the first microorganism into the culture medium.

According to another aspect of the present invention, there is provided a method for preparing biofuels including preparing an ethanol fermented solution by fermenting hexose from a mixture of pentose and hexose, separating and purifying the ethanol fermented solution, preparing a culture medium containing a fermentation waste generated by the separating and the purifying, inoculating a first microorganism into the culture medium, and culturing the first microorganism on the culture medium.

The mixture of pentose and hexose may be obtained by physically and chemically pre-processing and saccharifying at least one selected from the group consisting of lignocellulosic biomass and cellulosic biomass. The fermentation waste may contain at least one sugar selected from the group consisting of hexose including glucose, galactose and mannose, and pentose including xylose and arabinose.

In the method for preparing biofuels according to an embodiment of the present invention, the first microorganism may include at least one selected from the group consisting of yeast, *Clostridium, Colon bacillus, Bacillus, Anaeromyxobacter, Alcaligenes, Bacteroides, Escherichia, Lactobacillus, Lactococcus, Pichia, Pseudomonas, Ralstonia, Rhodococcus, Saccharomyces, Streptomyces, Thermus thermophilus (Thermus), Thermotoga, Thermoanaerobacter, Klebsiella*, Streptomycetaceae, Actinomycetaceae, *Colinebacterium, Zymomonas, Actinobacillus, Anaerobiospirillum*, and *Mannheimia*. The first microorganism may be cultured on the culture medium in at least one operation selected from the group consisting of batch, fed-batch, and continuous operations, and the method may further include separating and purifying the produced biofuels after culturing the first microorganism on the culture medium.

The biofuels may be bio-gas, alcohol, an alkane-based compound, or an alkene-based compound that can be used as fuels. The bio-gas may include methane and hydrogen. The alcohol may include ethanol, propanol, butanol, pentanol, and hexanol.

According to an aspect of the present invention, there is provided a method for preparing biochemicals including preparing a culture medium containing a fermentation waste generated in the alcohol production, inoculating a second microorganism into the culture medium, and culturing the second microorganism on the culture medium.

According to another aspect of the present invention, there is provided a method for preparing biochemicals including preparing an ethanol fermented solution by fermenting hexose from a mixture of pentose and hexose, separating and purifying the ethanol fermented solution, preparing a culture medium containing a fermentation waste generated in the separation and purification, inoculating a second microorganism into the culture medium, and culturing the second microorganism on the culture medium.

The mixture of pentose and hexose may be obtained by physically and chemically pre-processing and saccharifying at least one selected from the group consisting of lignocellulosic biomass and cellulosic biomass. The fermentation waste may contain at least one sugar selected from the group consisting of hexose including glucose, galactose and mannose, and pentose including xylose and arabinose.

In the method for preparing biochemicals according to an embodiment of the present invention, the second microorganism may include at least one selected from the group consisting of yeast, *Clostridium, Colon bacillus, Bacillus, Anaeromyxobacter, Alcaligenes, Bacteroides, Escherichia, Lactobacillus, Lactococcus, Pichia, Pseudomonas, Ralstonia, Rhodococcus, Saccharomyces, Streptomyces, Thermus, Thermotoga, Thermoanaerobacter, Klebsiella*, Streptomycetaceae, Actinomycetaceae, *Colinebacterium, Zymomonas, Actinobacillus, Anaerobiospirillum*, and *Mannheimia*.

The biochemicals may include at least one selected from the group consisting of amino acids, organic acids, yeast, biodegradable polymers, and an alcohol. The amino acids may include methionine and threonine. The organic acids may include at least one selected from the group consisting of lactic acid, butyric acid, succinic acid, and hydroxypripionic acid. The biodegradable polymers may include biopolyester.

Effect of the Invention

According to the method for preparing biofuels and biochemicals according to the present invention, the fermentation waste generated in the alcohol production is used as a culture medium for microorganisms to prepare biofuels and biochemicals in an economical and environmentally friendly way.

As the fermentation waste generated in the alcohol production is used as a culture medium for microorganisms, it is possible to reduce or eliminate the use of a variety of chemicals and nutrient components added to a conventional culture medium.

Also, it is possible to reduce an amount of a conventional carbon source used such as glucose, sucrose, glycerol, and the like. In addition, since the microorganism is sterilized during alcohol distillation, it is possible to reduce a great deal of energy costs involved in sterilization.

Furthermore, both hexose and pentose derived from lignocellulosic biomass are effectively used in the microorganism fermentation, thereby remarkably reducing a feedstock cost.

Accordingly, the method for preparing biofuels and biochemicals according to the present invention may remarkably reduce the feedstock cost and the energy cost involved in the preparation process. Also, the method of the present invention may have effects of environmental protection and resource savings, by recycling the waste generated in the alcohol fermentation and making use of both hexose and pentose.

The present invention provides a method for preparing biofuels and biochemicals that may efficiently make use of lignocellulosic biomass and reduce a cost of wastewater treatment and an additional nutrient component as well as energy involved in the preparing process.

BRIEF DESCRIPTION OF DRAWINGS

FIG. 13 is a graph illustrating a comparison of concentrations of butyric acid produced by *Clostridium tyrobutyricum* ATCC 25755 strain.

BEST MODE FOR CARRYING OUT THE INVENTION

Studies are being conducted on recycling a by-product produced in microorganism fermentation, but are very limited in that only some components of a substance produced as a by-product are selectively separated and then recycled. To date, few, if any, attempts are being made at preparing biofuels and biochemicals by using a fermentation waste generated in alcohol production as a culture medium for microorganisms.

Hereinafter the present invention is described in more detail with reference to the accompanying drawings.

A method for preparing biofuels according to an embodiment of the present invention may include preparing a culture medium containing a fermentation waste generated in alcohol production, inoculating a first microorganism into the culture medium, and culturing the first microorganism on the culture medium.

A method for preparing biochemicals according to another embodiment of the present invention may include preparing a culture medium containing a fermentation waste generated in alcohol production, inoculating a second microorganism into the culture medium, and culturing the second microorganism on the culture medium.

Figure 1:
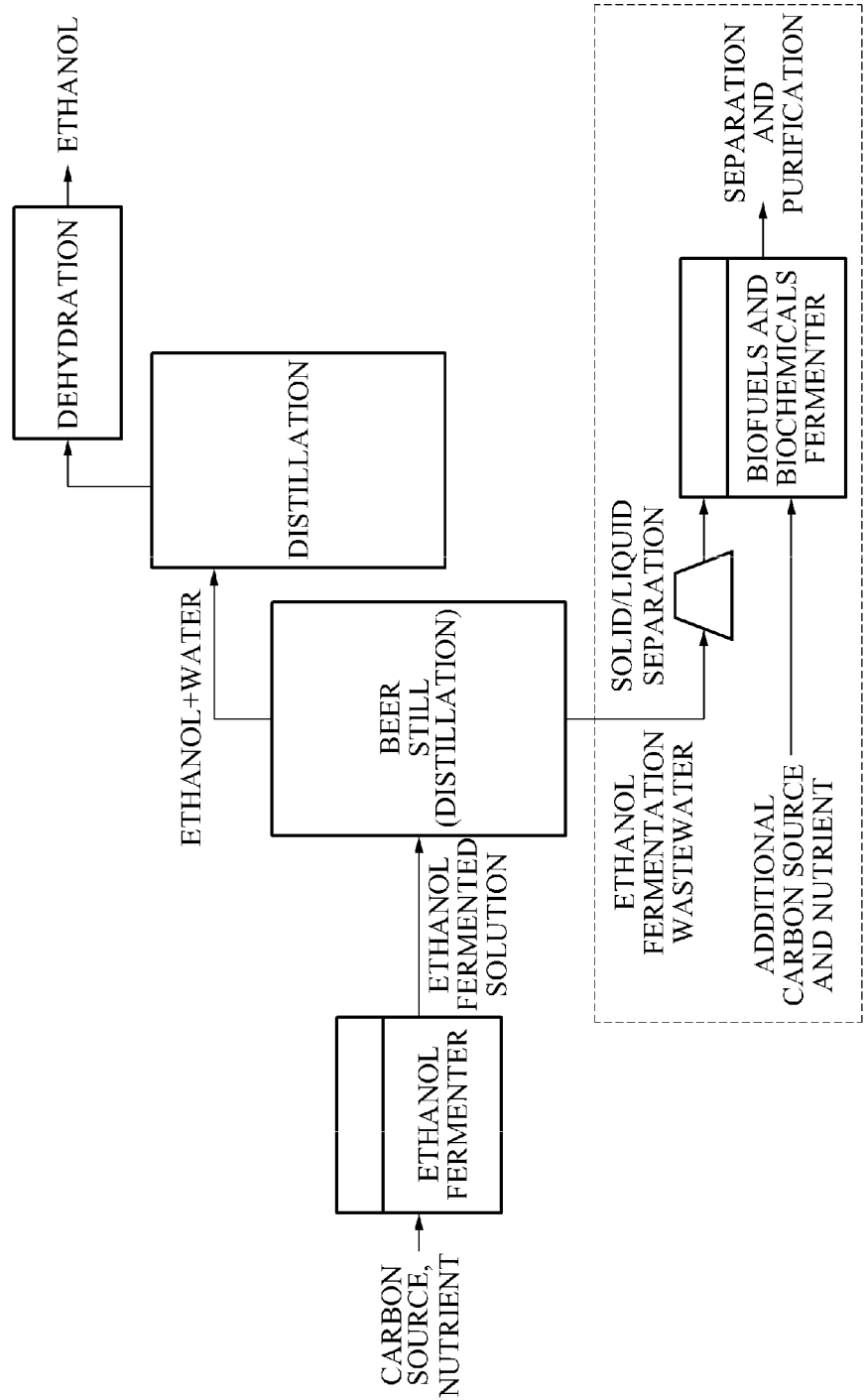
FIG. 1 is a diagram illustrating a process for preparing biofuels and biochemicals according to an embodiment of the present invention.

FIG. 1 is a diagram illustrating a process for preparing biofuels and biochemicals according to an embodiment of the present invention. Referring to FIG. 1, a fermented solution is prepared through microorganism fermentation in an ethanol fermenter. Various microorganisms are known to be capable of producing ethanol, but a microorganism being mainly used in the industrial field, at present, is *Saccharomyces cerevisiae*, that is a species of yeast. Also, various carbon sources may be used in ethanol fermentation. A microorganism capable of producing ethanol is implanted into a culture medium containing a carbon source generated through pre-processing of biomass, followed by fermentation in a batch, fed-batch, or continuous operation.

The resulting fermented solution is transferred to a distillation tower where ethanol is distilled and then recovered in an ethanol storage tank. Ethanol distillation takes place by increasing the temperature of the fermented medium to between 80 and 90° C., so that ethanol having a purity of about 95% or more is obtained and recovered. To obtain ethanol of a higher purity, a separate hydration process is required. In a general fermentation process, carbon dioxide gas is generated as a by-product, and after capture/compression, may be used for beverage or industrial use.

After ethanol is recovered in the ethanol storage tank, a fermentation waste remains. The fermentation waste is microorganisms killed during ethanol distillation at high temperature of 80° C. to 90° C., non-hydrolyzed solid carbohydrate residues, or non-fermented sugars. The fermentation waste is generated in the production of alcohol through fermentation after inoculating the microorganism capable of producing alcohol into the culture medium containing the carbon source.

The fermentation waste may be spread directly on the farmland as a compost to grow plants for agriculture or forestry, or may be used as a feed for domesticated animals. However, when the fermentation waste is directly spread on the farmland, there are soil and water contamination hazards. To use the fermentation waste as a feed for domesticated animals, the fermentation waste needs to be dehydrated at high temperature to obtain a solid concentrate. This dehydration requires a great deal of energy. Since the fermentation waste generated after distillation contains a sufficient amount of nutrient components necessary for a culture medium for microorganisms, the use of the fermentation waste as a culture medium may remarkably reduce costs related to nutrient components to be added when preparing a conventional culture medium. Also, since sugars remaining in the fermentation waste can be used as a carbon source, it is possible to reduce a cost of a carbon source necessary for microorganism cultivation. Since the microorganisms are sterilized at a high temperature during distillation, when the fermentation waste is used directly as a culture medium, a need to sterilize the culture medium at high temperature is unnecessary, and accordingly, a great deal of energy costs involved in the sterilization of a culture medium can be saved.

By transferring the fermentation waste without solids that have been separated by a solid/liquid separator to a biofuels and biochemicals fermenter or by transferring the fermentation waste with solids to a biofuels and biochemicals fermenter, directly without transferring to a solid/liquid separator, the fermentation waste is prepared as a culture medium for producing biofuels and biochemicals according to the present invention. As deemed necessary, water, a carbon source, and a nutrient component may be added to the biofuels and biochemicals fermenter. Glucose or all carbon sources usable in the cultivation of microorganism may be used as the carbon source. All materials capable of promoting the microorganism growth after addition to the culture medium may be used as the nutrient component.

The microorganism capable of producing biofuels and biochemicals is implanted into the culture medium. The first microorganism capable of producing biofuels and the second microorganism capable of producing biochemicals may include yeast, *Clostridium, Colon bacillus, Bacillus, Anaeromyxobacter, Alcaligenes, Bacteroides, Escherichia, Lactobacillus, Lactococcus, Pichia, Pseudomonas, Ralstonia, Rhodococcus, Saccharomyces, Streptomyces, Thermus, Thermotoga, Thermoanaerobacter, Klebsiella*, Streptomycetaceae, Actinomycetaceae, *Colinebacterium, Zymomonas, Actinobacillus, Anaerobiospirillum*, and *Mannheimia*, and wild type strains, mutant strains and recombinant strains thereof.

The microorganism is cultured on the culture medium in a batch, fed-batch, or continuous operation. After biofuels and biochemicals are produced through microorganism cultivation, the resulting biofuels and biochemicals are separated and purified, and then recovered. The biofuels may be used as they are or used as an additive added to biofuels. The biofuels may include bio-gas, an alcohol, an alkane-based compound, and an alkene-based compound. The biogas may include methane and hydrogen. The alcohol may include ethanol, propanol, butanol, pentanol, and hexanol. The biochemicals may be used as a feedstock for producing chemicals or an additive added to a feedstock, and include amino acids, organic acids, yeast, biodegradable polymers, and an alcohol that can be produced through microorganism cultivation. The amino acids may include methionine and threonine. The organic acids may include lactic acid, butyric acid, succinic acid, and hydroxypripionic acid. The biodegradable polymers may include biopolyester.

According to an embodiment of the present invention, the biofuels and the biochemicals may be efficiently prepared by the integrated fermentation of major sugars extracted from lignocellulosic biomass, such as pentose and hexose.

Figure 11:
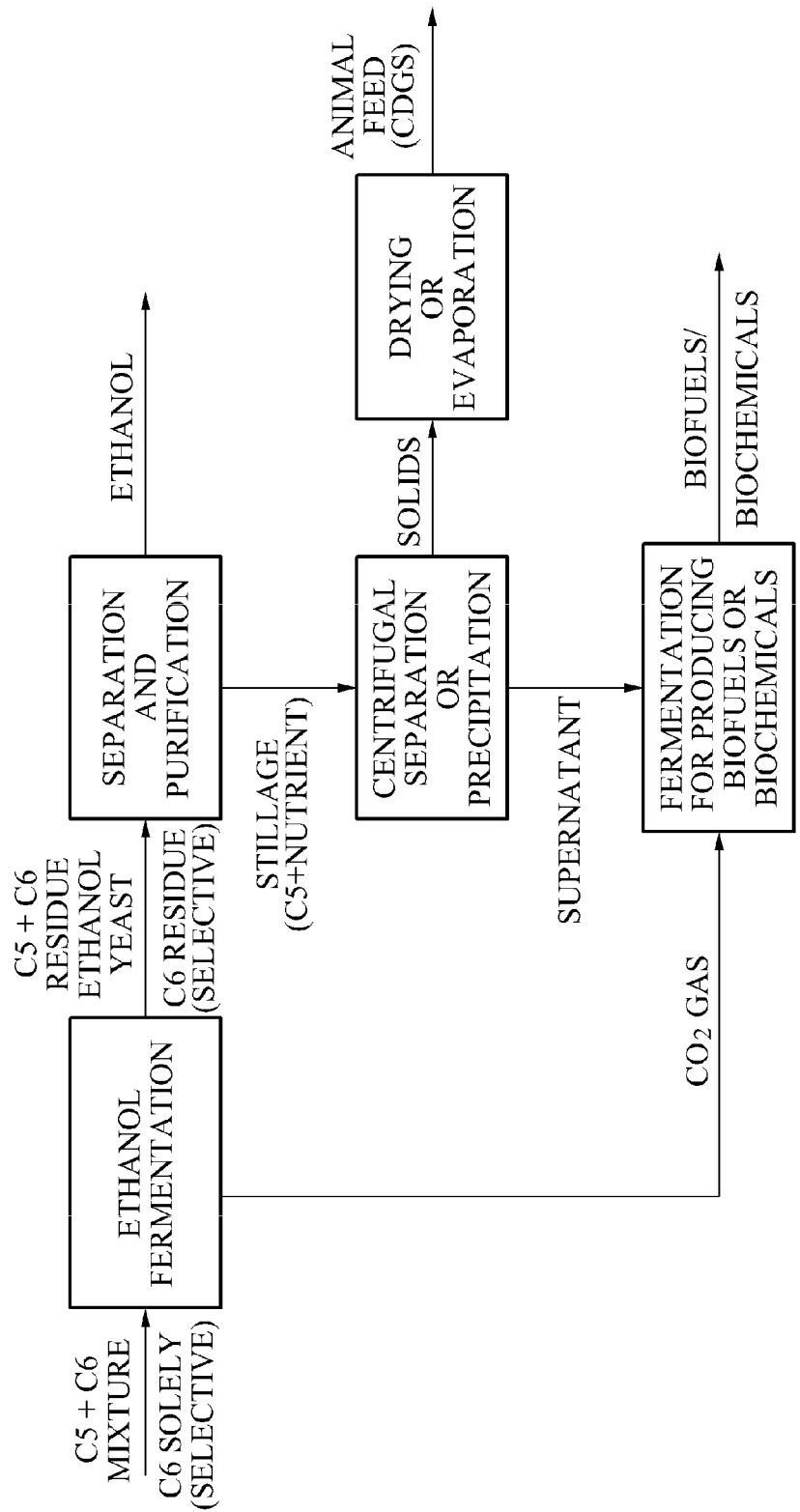
FIG. 11 is a diagram illustrating a process for preparing biofuels and biochemicals according to an embodiment of the present invention.

FIG. 11 is a diagram illustrating a process for preparing biofuels and biochemicals according to an embodiment of the present invention.

Referring to FIG. 11, lignocellulosic biomass is physically and chemically pre-processed, followed by hydrolysis using yeast, to yield a mixed saccharified solution of pentose and hexose. During ethanol fermentation, the hexose is consumed, and through separation and purification, ethanol is produced. Subsequent to fermentation, ethanol is removed through distillation. Biofuels and biochemicals are prepared using a fermentation waste containing the remaining pentose. The pentose may be used in the fermentation of butanol, butyric acid, or succinic acid to provide a carbon source and a nutrient component.

Generally, since a commercial ethanol yeast is either incapable of or has a remarkably low capability of utilizing pentose as a carbon source, an additional process for developing a strain is needed, for example, gene manipulation, to use the remaining pentose. In a case in which pentose and hexose coexist, a majority of strains capable of consuming pentose during production of biofuels and biochemicals do not consume pentose until hexose is completely consumed, or consume pentose in a mixed saccharified solution at a remarkably lower rate than when only pentose exists as a sole carbon source. Accordingly, difficulty exists in using a saccharified solution of lignocellulosic biomass from which both pentose and hexose are produced.

Through the linked processes described in the foregoing, the present invention may efficiently make use of lignocellulosic biomass by consuming hexose and pentose sequentially and thus, reduce the costs of energy, waste treatment, and an additional nutrient component involved in the preparation process.

Hereinafter, embodiments of the present invention will be described in more detail. However, it should be noted that descriptions proposed herein are simply examples preferable for the purpose of illustration only, and are not intended to limit the scope of the invention.

Embodiment

Recovery of Fermentation Waste and Elemental Analysis

A fermentation waste was directly obtained from an industrial ethanol factory of Changhae ethanol Co., Ltd. which is specialized in producing ethanol on an industrial scale. Changhae ethanol Co., Ltd. produces and sells commercial ethanol having a purity of 95% or more by yielding about 100 grams/liter (g/L) of ethanol through cultivation of *Saccharomyces cerevisiae* strain for producing ethanol and distilling a fermentation culture at a temperature in a range of 80° C. to 90° C. The fermentation waste with solids recovered from the industrial ethanol factory after ethanol distillation was used in the following embodiment.

After the fermentation waste was centrifugally separated at 12,000 revolutions per minute (rpm), for 10 minutes at 4° C., the concentrations of ethanol, acetic acid, and glucose present in the supernatant were analyzed using gas chromatography (GC) and high performance liquid chromatography (HPLC). GC and HPLC were also used in analyzing the concentrations of ethanol, butanol, butyric acid, and lactic acid produced through microorganism cultivation in the following embodiment. To test the starch present in the solids, 100 milliliters (ml) of 5% hydrochloric acid (HCl) was added to 50 ml of the sample, followed by acid saccharification for 2.5 hours at 95° C. and cooling. The acid saccharified solution was neutralized with 28% sodium hydroxide (NaOH), and then a total amount of sugar present in the fermentation waste was analyzed using HPLC. A concentration of proteins was analyzed using a total protein kit (Cat. No. TP0200) of Sigma-Aldrich.

The characteristics obtained by analyzing the fermentation waste recovered from the factory of Changhae ethanol Co., Ltd. are shown in Table 1.

TABLE 1

| Component | Concentration |
| --- | --- |
| Ethanol | 0.0 g/L |
| Acetic acid | 2.1 g/L |
| Protein | 2.0 mg/ml |
| Sugar in liquid state | 4.0 g/L |
| Total sugar (containing solids) | 6.8 g/L |

Production of Biofuels Using Culture Medium Containing Fermentation Waste (1) Production of Biobutanol Using *Clostridium Acetobutylicum* Strain A. Production of Biobutanol Through Direct Utilization of Fermentation Waste The fermentation waste recovered from the industrial ethanol factory of Changhae ethanol Co., Ltd. was used as a culture medium, and in this instance, a culture medium containing fermentation waste without solids and a culture medium containing the fermentation waste with solids were each used as a culture medium for butanol production. A strain of *Clostridium acetobutylicum* ATCC 824 was cultured in a 6.6 liter (L) bioreactor in a batch operation. To determine the characteristics of the fermentation waste as a culture medium for butanol production, a *Clostridium* culture medium conventionally used in culturing a strain of *Clostridium* was used as a control. Also, a culture medium prepared by mixing the *Clostridium* culture medium with the fermentation waste at a volumeric ratio of 50:50 was used as a culture medium for butanol production.

To culture a strain of *Clostridium acetobutylicum* ATCC 824, 200 mL of a liquid culture was implanted into a bioreactor including each of the culture medium containing the fermentation waste without solids in which the solids were removed from 2.0 L of the fermentation waste recovered from the industrial ethanol factory of Changhae ethanol Co., Ltd., the culture medium containing the fermentation waste with solids, the *Clostridium* culture medium, and the culture medium prepared by mixing the *Clostridium* culture medium with the fermentation waste at a volumeric ratio of 50:50. In this instance, culture conditions were set such that an initial glucose concentration was 40 g/L, an initial pH was 6.0, a culture temperature was 37° C., and a stirring rate was 150 rpm. To maintain the anaerobic condition during cultivation, nitrogen gas was continuously supplied at a flow rate of 50 ml/min, and a pH was adjusted to 5.0 or more using 28% (w/v) ammonia solution during cultivation.

When the culture medium containing the fermentation waste was used, the *Clostridium* culture medium was used, and the culture medium prepared by mixing the *Clostridium* culture medium with the fermentation waste at a volumeric ratio of 50:50 was used, after 70 hours of cultivation, the *Clostridium acetobutylicum* ATCC 824 strain completely consumed the 40 g/L of glucose added to the culture medium.

Figure 2:
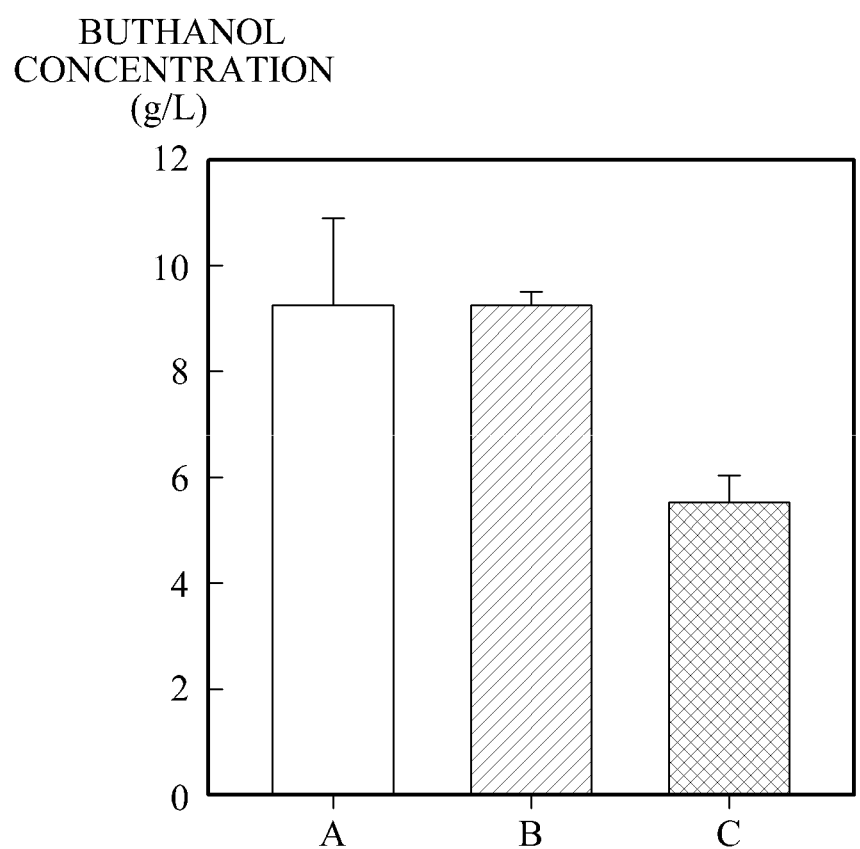
FIG. 2 is a graph illustrating a comparison of concentrations of butanol produced by *Clostridium acetobutylicum* ATCC 824 strain.

FIG. 2 is a graph illustrating a comparison of concentrations of butanol produced by the *Clostridium acetobutylicum* ATCC 824 strain. Referring to FIG. 2, the concentration of butanol produced by the *Clostridium acetobutylicum* ATCC 824 strain on the culture medium (A) containing the fermentation waste without solids, in which the solids were removed from the fermentation waste generated in the ethanol production and the culture medium (B) containing the fermentation waste with solids was 9.2±1.7 g/L. The concentration of butanol produced on the *Clostridium* culture medium (C) used as a control was 5.5±0.6 g/L.

Figure 3:
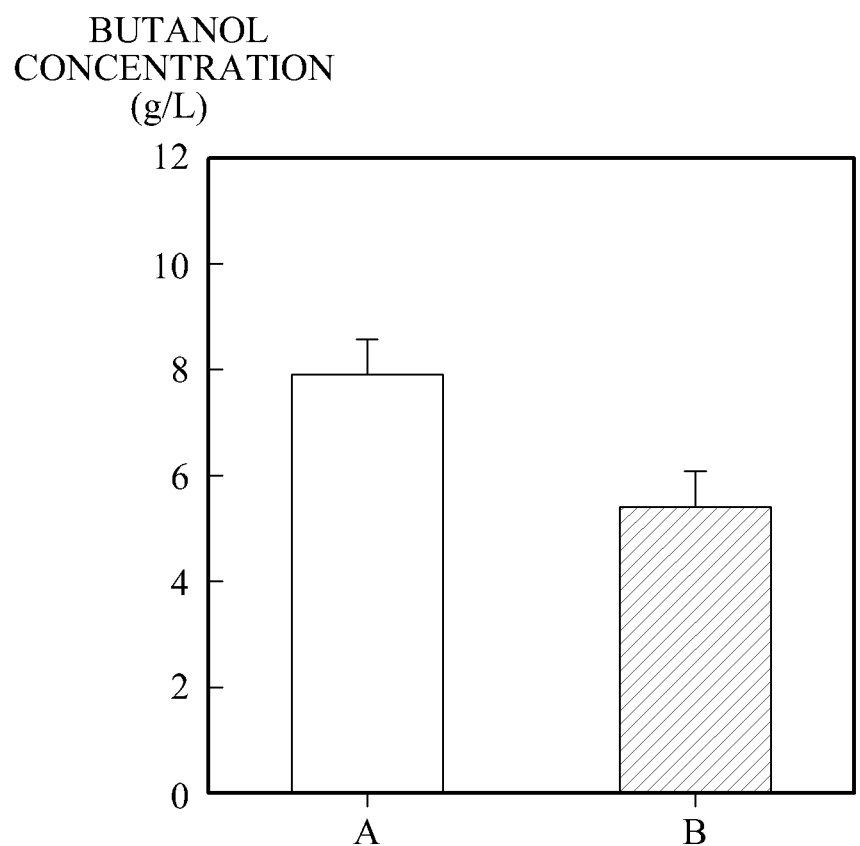
FIG. 3 is a graph illustrating a comparison of concentrations of butanol produced by *Clostridium acetobutylicum* ATCC 824 strain.

FIG. 3 is a graph illustrating a comparison of concentrations of butanol produced by the *Clostridium acetobutylicum* ATCC 824 strain. Referring to FIG. 3, the concentration of butanol produced on the culture medium (A) prepared by mixing the *Clostridium* culture medium with the fermentation waste at a volumeric ratio of 50:50 was 7.4±0.7 g/L. In this instance, the concentration is higher than the concentration of butanol produced on the *Clostridium* culture medium (B) used as a control, that is, 5.5±0.6 g/L.

From this result, it was found that the fermentation waste exhibited at least 67% improvement in the butanol production when compared with the *Clostridium* culture medium conventionally used in the production of butanol.

B. Production of Biobutanol Using Autolysis of Fermentation Waste

An autolysate produced by autolysis of the fermentation waste recovered from the industrial ethanol factory of Changhae ethanol Co., Ltd. was used as a culture medium for butanol production. The ethanol fermentation waste was autolyzed by a batch reaction at 50° C. for a period of 24 hours. A strain of *Clostridium acetobutylicum* ATCC 824 was cultured in a 6.6 L bioreactor in a batch operation. To determine the characteristics of the fermentation waste as a culture medium for butanol production, a *Clostridium* culture medium conventionally used in culturing a strain of *Clostridium* was used as a control.

To culture a strain of *Clostridium acetobutylicum* ATCC 824, after the autolysate of the fermentation waste recovered from the industrial ethanol factory of Changhae ethanol Co., Ltd. was centrifugally separated at 12,000 rpm at 4° C., 200 ml of a liquid culture was implanted into a bioreactor including each of a culture medium containing 1.0 L of the supernatant and the *Clostridium* culture medium. In this instance, the culture conditions were set such that an initial glucose concentration was 60 g/L, an initial pH was 6.0, a culture temperature was 37° C., and a stirring rate was 150 rpm. To maintain the anaerobic condition during cultivation, nitrogen gas was continuously supplied at a flow rate of 50 mL/min, and a pH was adjusted to 5.0 or more using 28% (w/v) ammonia solution during cultivation.

When the autolysate of the fermentation waste was used as a culture medium and the *Clostridium* culture medium was used, after 72 hours of cultivation, the *Clostridium acetobutylicum* ATCC 824 strain completely consumed the 60 g/L of glucose added to the culture medium.

Figure 4:
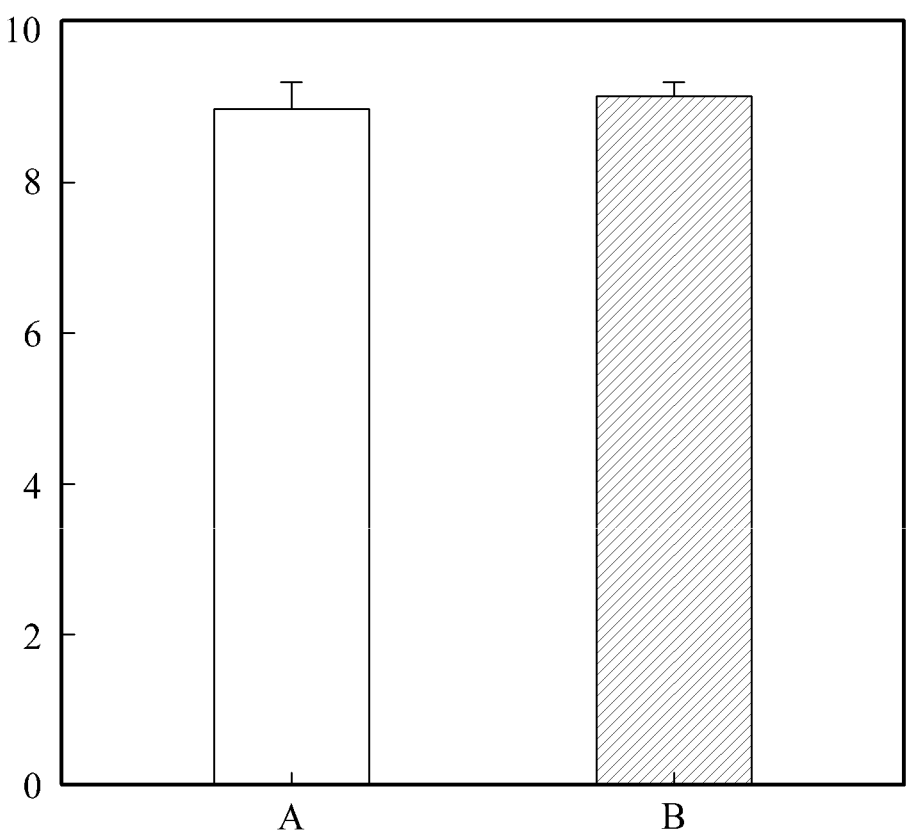
FIG. 4 is a graph illustrating a comparison of concentrations of butanol produced by *Clostridium acetobutylicum* ATCC 824 strain.

FIG. 4 is a graph illustrating a comparison of concentrations of butanol produced by the *Clostridium acetobutylicum* ATCC 824 strain. Referring to FIG. 4, when the autolysate of the ethanol fermentation waste was used as a culture medium (A), the concentration of butanol was 8.9±0.3 g/L that is almost equal to the concentration of butanol produced on the *Clostridium* culture medium (B) used as a control, that is, 9.0±0.1 g/L.

Accordingly, it was found through this result that the fermentation waste can be used as a culture medium as is, or after autolysis.

(2) Production of Biobutanol Using *Clostridium Beijerinckii* Strain

By using a culture medium containing the fermentation waste without solids in which the solids were removed from the fermentation waste recovered from the industrial ethanol factory of Changhae ethanol Co., Ltd., a strain of *Clostridium beijerinckii* NCIMB 8052 was cultured in a 6.6 L bioreactor in a batch operation. To determine the characteristics of the fermentation waste as a culture medium for butanol production through microorganism cultivation, a *Clostridium* culture medium conventionally used in culturing a strain of *Clostridium* was used as a control.

To culture a strain of *Clostridium beijerinckii* NCIMB 8052, 200 mL of a liquid culture was implanted into a bioreactor including each of the culture medium containing the fermentation waste without solids in which the solids were removed from 2.0 L of the fermentation waste recovered from the industrial ethanol factory of Changhae ethanol Co., Ltd. and the *Clostridium* culture medium. In this instance, the culture conditions were set such that an initial glucose concentration was 60 g/L, an initial pH was 6.0, a culture temperature was 37° C., and a stirring rate was 150 rpm. To maintain the anaerobic condition during cultivation, nitrogen gas was continuously supplied at a flow rate of 50 mL/min, and a pH was adjusted to 5.0 or more using 28% (w/v) ammonia solution during cultivation. After 24 hours of cultivation, an amount of glucose consumption was 20 g/L when the culture medium containing the fermentation waste without solids was used, and an amount of glucose consumption was 30 g/L when the *Clostridium* culture medium was used.

Figure 5:
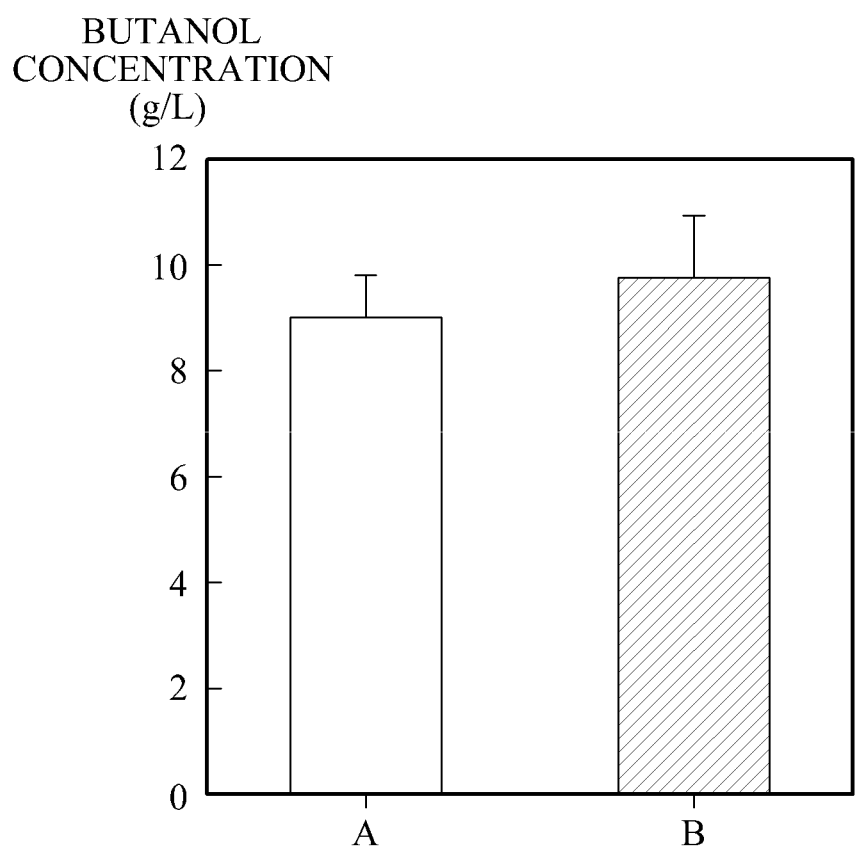
FIG. 5 is a graph illustrating a comparison of concentrations of butanol produced by *Clostridium beijerinckii* NCIMB 8052 strain.

FIG. 5 is a graph illustrating a comparison of concentrations of butanol produced by the *Clostridium beijerinckii* NCIMB 8052 strain. Referring to FIG. 5, when the culture medium (A) containing the fermentation waste without solids in which the solids were removed from the fermentation waste generated in the ethanol production was used, the concentration of butanol was 9.2±0.7 g/L, and when the *Clostridium* culture medium (B) was used, the concentration of butanol was 9.8±1.0 g/L.

(3) Production of Bioethanol

The fermentation waste recovered from the industrial ethanol factory of

Changhae ethanol Co., Ltd. was used as a culture medium, and in this instance, a culture medium containing the fermentation waste without solids and a culture medium containing the fermentation waste with solids were each used as a culture medium for ethanol production. A strain of *Saccharomyces cerevisiae* ATCC 2601 was cultured in a 250 mL flask. To determine the characteristics of the fermentation waste, as a culture medium for ethanol production through microorganism cultivation, a yeast mold medium (YM Broth, Difco, Cat. No. 271120) conventionally used as a culture medium for ethanol fermentation was used as a control. The components of the yeast mold medium and content thereof are shown in Table 2.

TABLE 2

| Component | Content (g/L) |
|---|---|
| Yeast extract | 2.1 |
| Malt extract | 2.0 |
| Peptone | 4.0 |
| Dextrose | 6.8 |

To culture a strain of Saccharomyces cerevisiae ATCC 2601, 3 mL of a liquid culture was implanted into a flask including each of the culture medium containing the fermentation waste without solids in which the solids were removed from 100 mL of the fermentation waste recovered from the industrial ethanol factory of Changhae ethanol Co., Ltd., the culture medium containing the fermentation waste with solids, and the YM medium. In this instance, an initial concentration of glucose as a carbon source was adjusted to 40 g/L. Also, an initial pH of the culture medium was adjusted to 5. A shaking incubator capable of adjusting the temperature was used in the cultivation, and the culture temperature was adjusted to 30° C. and the stirring rate was adjusted to 200 rpm.

When the fermentation waste was used as a culture medium and the YM medium was used, after 24 hours of cultivation, the Saccharomyces cerevisiae ATCC 2601 strain completely consumed the 40 g/L of glucose added to the culture medium.

Figure 6:
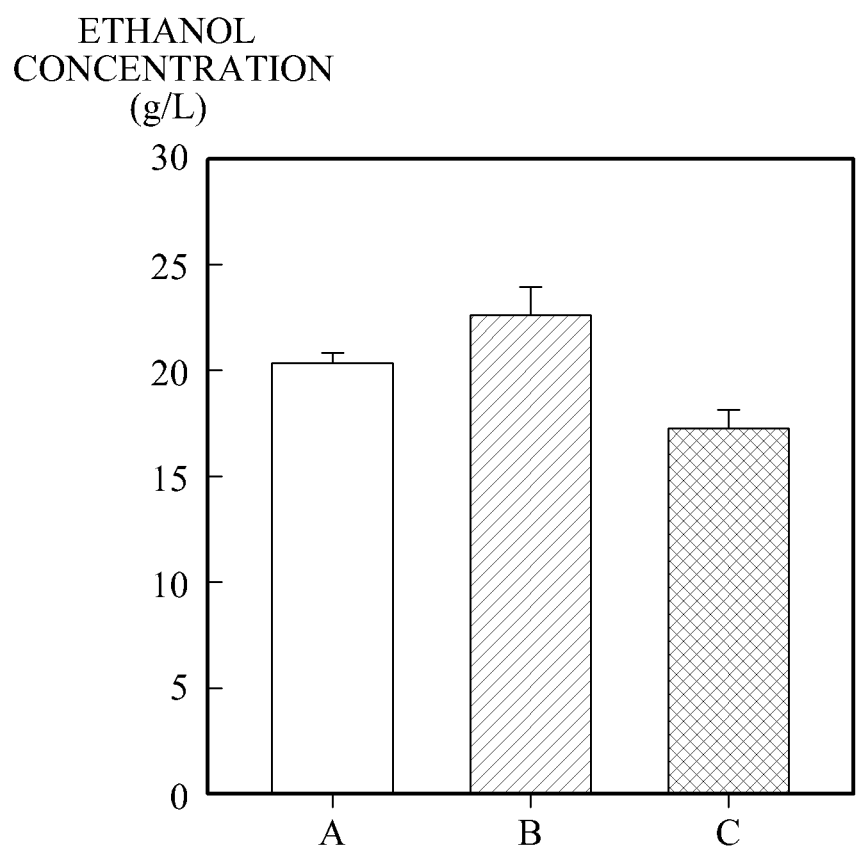
FIG. 6 is a graph illustrating a comparison of concentrations of ethanol produced by *Saccharomyces cerevisiae* ATCC 2601 strain.

FIG. 6 is a graph illustrating the comparison of concentrations of ethanol produced by the Saccharomyces cerevisiae ATCC 2601 strain. Referring to FIG. 6, the concentration of ethanol produced on the culture medium (A) containing the fermentation waste without solids in which the solids were removed from the fermentation waste generated in the ethanol production and the culture medium (B) containing the fermentation waste with solids was 20.5±0.3 g/L and 23.5±1.3 g/L, respectively. The concentration of ethanol produced on the YM medium (C) conventionally used in the production of ethanol was 17.7±0.7 g/L. From this result, it was found that the culture medium according to the present invention exhibited at least a 15% improvement in the ethanol production when compared to the YM medium conventionally used in the production of ethanol.

Production of Biochemicals Using Culture Medium Containing Fermentation Waste (1) Production of Butyric Acid By using a culture medium containing the fermentation waste without solids in which the solids were removed from the fermentation waste recovered from the industrial ethanol factory of Changhae ethanol Co., Ltd., a strain of Clostridium tyrobutyricum ATCC 25755 was cultured in a 6.6 L bioreactor in a batch operation. To determine the characteristics of the fermentation waste as a culture medium for butyric acid production through microorganism cultivation, a Clostridium culture medium conventionally used in culturing a strain of Clostridium was used as a control.

To culture a strain of Clostridium tyrobutyricum ATCC 25755, 200 mL of a liquid culture was implanted into a bioreactor including each of the culture medium containing the fermentation waste without solids in which the solids were removed from 2.0 L of the fermentation waste recovered from the industrial ethanol factory of Changhae ethanol Co., Ltd. and the Clostridium culture medium. In this instance, the culture conditions were set such that an initial glucose concentration was 40 g/L, a culture temperature was 37° C., and a stirring rate was 150 rpm. To maintain the anaerobic condition during cultivation, nitrogen gas was continuously supplied at a flow rate of 50 mL/min, and a pH was adjusted to 6.0 using 28% (w/v) ammonia solution during cultivation.

When the fermentation waste without solids was used as a culture medium and the Clostridium culture medium was used, after 22 hours of cultivation, the Clostridium tyrobutyricum ATCC 25755 strain completely consumed glucose added to the culture medium.

Figure 7:
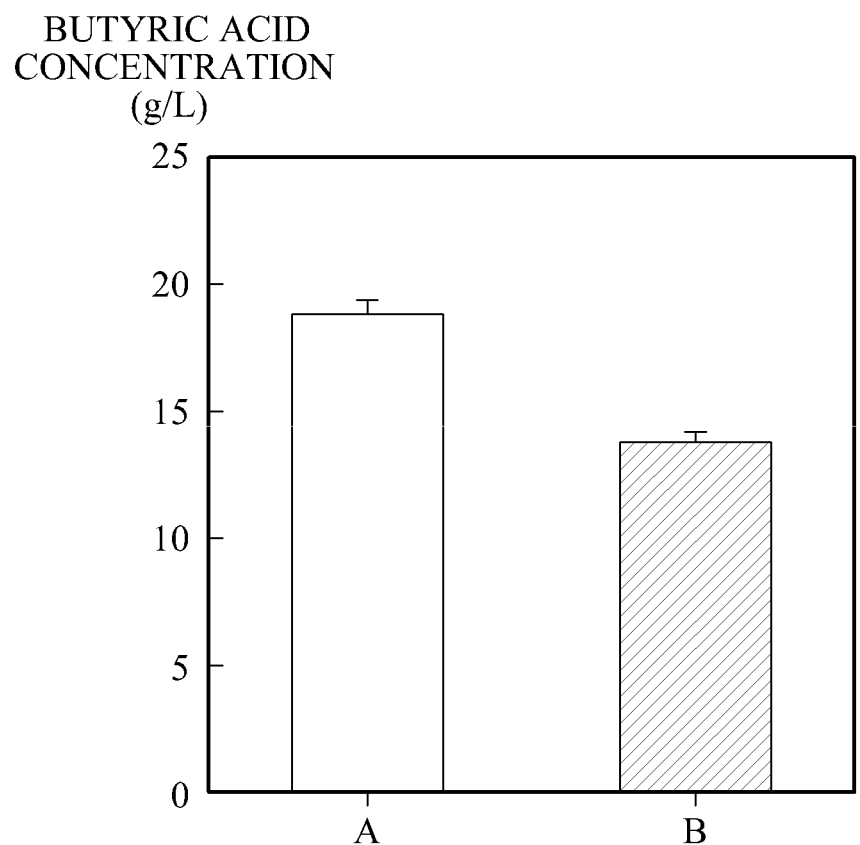
FIG. 7 is a graph illustrating a comparison of concentrations of butyric acid produced by *Clostridium tyrobutyricum* ATCC 25755 strain.

FIG. 7 is a graph illustrating a comparison of concentrations of butyric acid produced by the Clostridium tyrobutyricum ATCC 25755 strain. Referring to FIG. 7, the concentration of butyric acid produced on the culture medium (A) containing the fermentation waste without solids in which the solids were removed from the fermentation waste generated in the ethanol production was 19.0±0.5 g/L, and the concentration of butyric acid produced on the Clostridium culture medium (B) was 14.5±0.2 g/L. From this result, it was found that the fermentation waste exhibited at least a 31% improvement in the butyric acid production when compared to the Clostridium culture medium conventionally used in the production of butyric acid.

(2) Production of Lactic Acid

By using a culture medium containing the fermentation waste with solids recovered from the industrial ethanol factory of Changhae ethanol Co., Ltd. and a culture medium containing the fermentation waste without solids, a strain of Lactobacillus acidophilus NCFM was implanted into a 2.5 L fermenter including 1.5 L of a liquid culture and then cultured in a batch operation. To determine the characteristics of the fermentation waste as a culture medium for lactic acid production through microorganism cultivation, an MRS medium (MRS Broth, Difco, Cat. No. 288130) conventionally used for Lactobacillus cultivation was used as a control. The components of the MRS medium and content thereof are shown in Table 3.

TABLE 3

| Component | Content (g/L) |
|---|---|
| Proteose Peptone No. 3 | 10.0 |
| Beef Extract | 10.0 |
| Yeast Extract | 5.0 |
| Dextrose | 20.0 |
| Polysorbate 80 | 1.0 |
| Ammonium Citrate | 2.0 |
| Sodium Acetate | 5.0 |
| Magnesium Sulfate | 0.1 |
| Manganese Sulfate | 0.05 |
| Dipotassium Phosphate | 2.0 |

To carry out cultivation for producing lactic acid, 60 mL of a liquid culture of Lactobacillus acidophilus was implanted into 1.5 L of the culture medium. In this instance, an initial glucose concentration was adjusted to 50 g/L, and a culture temperature was 37° C. and a stirring rate was 200 rpm. Also, a pH for lactic acid production was adjusted to 6.5 using 10 M NaOH. Since a majority of strains for lactic acid production including Lactobacillus acidophilus strain are anaerobic bacteria, an anaerobic condition was not specifically set.

After 24 hours of cultivation, the Lactobacillus acidophilus NCFM strain completely consumed the initial glucose on each of the culture medium (A) containing the fermentation waste with solids, the culture medium (B) containing the fermentation waste without solids, and the MRS medium (C).

Figure 8:
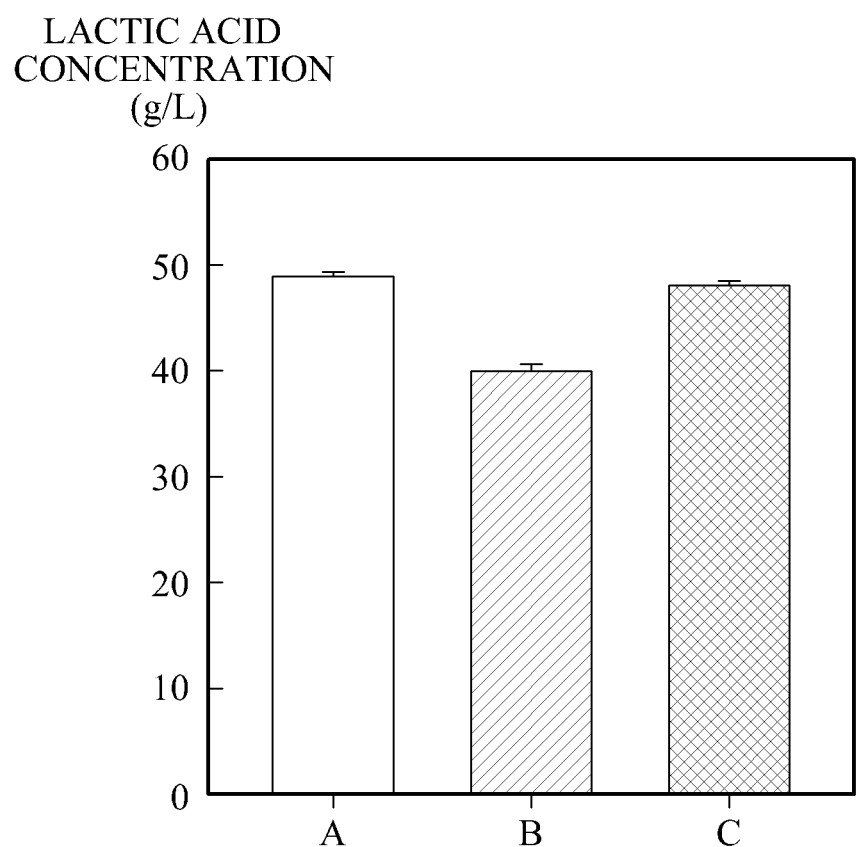
FIG. 8 is a graph illustrating a comparison of concentrations of lactic acid produced by *Lactobacillus acidophilus* NCFM strain.

FIG. 8 is a graph illustrating a comparison of concentrations of lactic acid produced by the Lactobacillus acidophilus NCFM strain. Referring to FIG. 8, the concentration of lactic acid produced on the culture medium (A) containing the fermentation waste with solids generated in the ethanol production was 48.2±0.4 g/L, the concentration of lactic acid produced on the culture medium (B) containing the fermentation waste without solids was 41.2±0.9 g/L, and the concentration of lactic acid produced on the MRS medium (C) was 47.2±0.5 g/L.

Referring to FIG. 8, it was found that when the fermentation waste generated in the ethanol production is used as a lactic acid fermentation medium, the fermentation waste can replace a lactic acid production medium irrespective of whether the solids were removed. In particular, when culturing a strain of Lactobacillus acidophilus for lactic acid production, a concentration of lactic acid produced on the culture medium containing the fermentation waste with solids in which the solids were not removed from the fermentation waste was higher.

(3) Production of Succinic Acid

An attempt was made to produce succinic acid by culturing a strain of Actinobacillus succinogenes ATCC 55618 in a 500 mL flask using a culture medium containing the fermentation waste without solids in which the solids were removed from the fermentation waste recovered from the industrial ethanol factory of Changhae ethanol Co., Ltd. To determine the characteristics of the fermentation waste as a culture medium for succinic acid production through microorganism cultivation, a culture medium of Table 4 was used as a control.

TABLE 4

| Component | Content (g/L) |
| --- | --- |
| Yeast Extract | 5.0 |
| NaHCO$_3$ | 10.0 |
| NaH$_2$PO$_4$•H$_2$O | 8.5 |
| K$_2$HPO$_4$ | 15.5 |
| Glucose | 18.0 |

To culture a strain of Actinobacillus succinogenes ATCC 55618, the solids were removed from the fermentation waste recovered from the industrial ethanol factory of Changhae ethanol Co., Ltd., and then components other than yeast extract in Table 4 were added to the fermentation waste without solids. In this instance, 10 ml of a liquid culture in a tube was inserted into a flask including 200 ml of the culture medium. After cultivation was carried out in the flask at 39° C. for 48 hours, the Actinobacillus succinogenes ATCC 55618 strain was implanted into a 6.5 L fermenter including 2 L of the liquid culture. 18 g/L of glucose was added to the culture medium as a carbon source. A pH of the fermenter was adjusted to 7.0 using 28% ammonia solution. During fermentation, 99.999% CO$_2$ was continuously purged at a rate of 0.05 volume per volume per minute (vvm) and a culture temperature was maintained at a temperature of 39° C.

After 40 hours of cultivation, the Actinobacillus succinogenes ATCC 55618 strain completely consumed the 18 g/L of glucose added to the culture medium.

Figure 9:
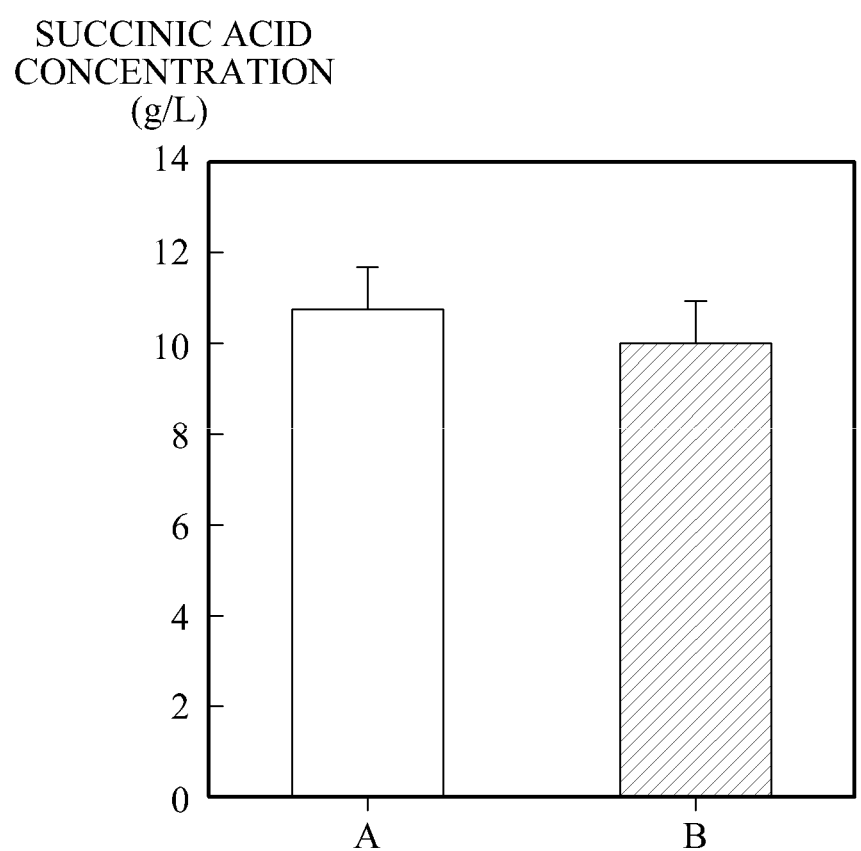
FIG. 9 is a graph illustrating a comparison of concentrations of succinic acid produced by *Actinobacillus succinogenes* ATCC 55618 strain.

FIG. 9 is a graph illustrating a comparison of concentrations of succinic acid produced by the Actinobacillus succinogenes ATCC 55618 strain. Referring to FIG. 9, the concentration of succinic acid produced on the culture medium (A) containing the fermentation waste generated in the ethanol production was 10.7±0.8 g/L. The concentration of succinic acid produced on the control (B) was 10.1±0.8 g/L. From this result, it was found that the production of succinic acid using the culture medium according to the preparing method of the present invention was greater than or equal to that of the control conventionally used in the production of succinic acid.

(4) Production of 3-Hydroxypropionic Acid

An attempt was made to produce 3-hydroxypropionic acid by culturing 50 ml of a recombinant strain developed to produce 3-hydroxypropionic acid, E. coli BL21_pCDFDuet_dhaB_gdrAB_EcoRI_AflII#15_pQE80L_Kp_aldH_BamHI_HindIII #2 strain in a 250 ml flask by using a culture medium containing the fermentation waste without solids in which the solids were removed from the fermentation waste recovered from the industrial ethanol factory of Changhae ethanol Co., Ltd. To determine the characteristics of the fermentation waste as a culture medium for 3-hydroxypropionic acid production through microorganism cultivation, a culture medium prepared by adding the components of Table 5 to M9 salts prepared to produce 3-hydroxypropionic acid was used as a control. 50 millimoles (mM) of glycerol was used as a carbon source.

TABLE 5

| Component | Concentration |
| --- | --- |
| IPTG concentration | 0.1 mM |
| Yeast extract | 0.2 g/L |
| Coenzyme B12 | 20 μM |
| Glycerol | 50 mM |

More specifically, a strain of E. coli was cultured on the culture medium containing 5% of the fermentation wastewater without solids in which the solids were removed from the fermentation waste recovered from the industrial ethanol factory of Changhae ethanol Co., Ltd. in place of yeast extract being used as a carbon source in the control, and on the control, respectively. In this instance, 5 ml of a liquid culture in a tube was implanted into a flask including 50 ml of each culture medium, and stirred at 200 rpm for 30 hours at 37° C.

Figure 10:
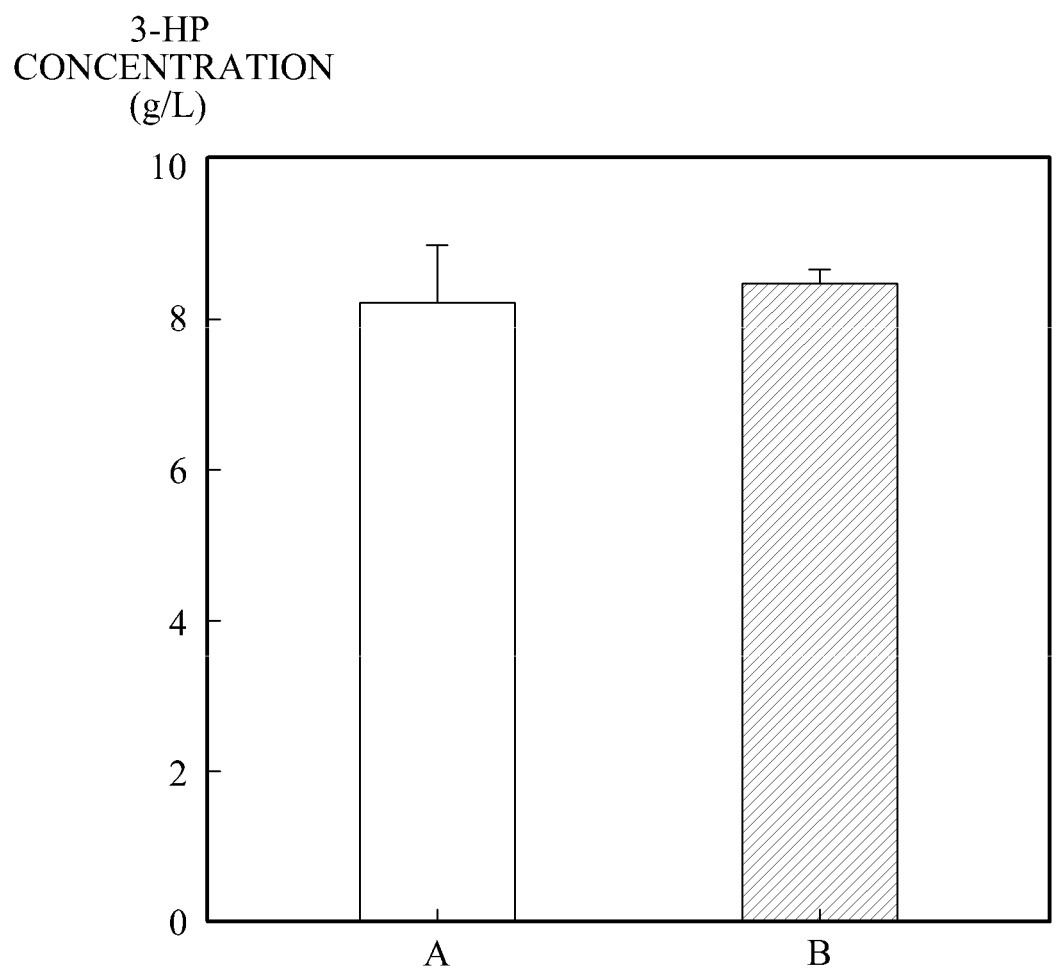
FIG. 10 is a graph illustrating a comparison of concentrations of 3-hydroxypropionic acid produced by *E. coli* strain.

FIG. 10 is a graph illustrating a comparison of concentrations of 3-hydroxypropionic acid produced by the E. coli strain. Referring to FIG. 10, the concentration of 3-hydroxypropionic acid produced on the culture medium (A) containing the fermentation waste generated in the ethanol production was 8.4±0.7 g/L, and the concentration of 3-hydroxypropionic acid produced on the control (B) was 8.6±0.0 g/L. This result means that the production of 3-hydroxypropionic acid using the culture medium prepared according to the present invention is almost equal to that of the control conventionally used in the production of 3-hydroxypropionic acid.

Pre-Processing and Ethanol Fermentation of Lignocellulosic Biomass

Barley straw offered by the National Institute of Crop Science, Rural Development Administration was used as a lignocellulosic biomass. Composition of the barley straw was 37.2% of cellulose, 22.4% of hemicellulose, 19.3% of lignin, and 1.7% of ash, as shown in Table 6 below.

TABLE 6

| Component | % Composition |
| --- | --- |
| Cellulose (Glucose) | 37.2 |
| Hemicellulose (xylose) | 22.4 |
| Lignin | 19.3 |
| Water | 7.9 |
| Ash | 1.7 |
| Others | 11.5 |

10% (w/v) of barley straw pulverized less than 1 millimeter (mm) by a crushing machine and a milling machine was immersed in 15% (v/v) ammonia solution, followed by reaction at 150° C. for 60 minutes.

Composition of the pre-processed barley straw was 54.8% of cellulose, 21.9% of hemicelluloses, and 12.7% of lignin. 250 grams (g) of the pre-processed barley straw was mixed with 1000 ml of 0.1 M sodium citrate buffer (pH 4.8) and 1000 ml of distilled water, and then 30 FPU/g of complex cellulose (Novozyme, NS50015) and 30 CBU/g of β-glucosidase (Novozyme, NS50010) were added. Subsequently, saccharification was carried out in a shaking incubator at 150 rpm, for a period of 72 hours at a temperature of 45° C.

After saccharification was completed, the saccharified solution contained 54.9 g/L of glucose and 25.1 g/L of xylose, and after pre-processing, was directly used as a culture medium for ethanol fermentation. The saccharified solution was added to a YPD medium containing 10 g/L of yeast extract, 20 g/L of protease peptone, and 10 g/L of dextrose, and then cultured in a shaking incubator at 120 rpm, for a period of 12 hours at a temperature of 32° C. to prepare a liquid culture of Saccharomyces cerevisiae CHY1011 strain. Here, 5% (v/v) of the liquid culture of Saccharomyces cerevisiae CHY1011 strain was implanted and then fermented in a shaking incubator at 150 rpm, for a period of 24 hours at a temperature of 32° C.

After ethanol fermentation was completed, 20.7 g/L of ethanol was produced and a sugar residue contained 0 g/L of glucose and 20.1 g/L of xylose. The ethanol fermented solution was evaporated at 89° C. under a reduced pressure so as to separate ethanol, and the remaining fermentation waste was used as a culture medium for producing biofuels or biochemicals.

Production of Biobutanol Using Fermentation Waste After Ethanol Fermentation

After the barley straw as lignocellulosic biomass underwent ethanol fermentation and distillation under the reduced pressure, the remaining fermentation waste was directly used as a culture medium for butanol fermentation as is, or used after centrifugal separation at 12,000 rpm for a period of 15 minutes.

After the fermentation waste was centrifugally separated at 12,000 rpm for 10 minutes at 4° C., the concentrations of ethanol, acetic acid, glucose, and xylose present in the supernatant were analyzed using GC and HPLC. GC and HPLC were also used in analyzing the concentrations of ethanol, butanol, butyric acid, and succinic acid produced through microorganism cultivation in the following embodiment. The total protein concentration was analyzed using a total protein kit (Sigma TP200, Micro-Lowry, Onishi & Barr Modification) of Sigma-Aldrich.

α-amino nitrogen was analyzed through USP XXI Procedure (1985). The characteristics of the ethanol fermentation waste analyzed by the above analysis method are shown in Table 7.

TABLE 7

| | |
|---|---|
| pH | 3.7 |
| Content of glucose (g/L) | 0 |
| Content of xylose (g/L) | 17 |
| Content of ethanol (g/L) | 0 |
| Total protein (mg/mL) | 1.3 |
| α-amino nitrogen (mg/mL) | 0.16 |

In the butanol fermentation using the ethanol fermentation waste as a culture medium, a strain of Clostridium beijerinckii ATCC35702 was used. In this instance, 50 ml of the ethanol fermentation waste was put in a 250 ml flask, and 2 ml of a liquid culture of Clostridium beijerinckii ATCC35702 strain was implanted into the culture medium. For cultivation, the culture medium was placed in an anaerobic chamber ($N_2$ 90%, $CO_2$ 5%, $H_2$ 5%) at 37° C. for a period of 60 hours.

As a control, a Clostridium culture medium containing, as a carbon source, xylose of the same concentration as the saccharified solution was used. The components of the Clostridium culture medium and content thereof are shown in Table 8.

TABLE 8

| Component | Content (g/L) |
|---|---|
| $KH_2PO_4$ | 0.75 |
| $K_2HPO_4$ | 0.75 |
| $MgSO_4 \cdot H_2O$ | 0.4 |
| $MnSO_4 \cdot H_2O$ | 0.01 |
| $FeSO_4 \cdot 7H_2O$ | 0.01 |
| NaCl | 1.0 |
| Asparagine | 2.0 |
| Yeast Extract | 5.0 |
| $(NH_4)_2SO_4$ | 2.0 |

When the ethanol fermentation waste containing pentose was used as a culture medium and the Clostridium culture medium was used, the Clostridium beijerinckii ATCC 35702 strain completely consumed the 17 g/L of xylose within a period of 60 hours of cultivation.

Figure 12:
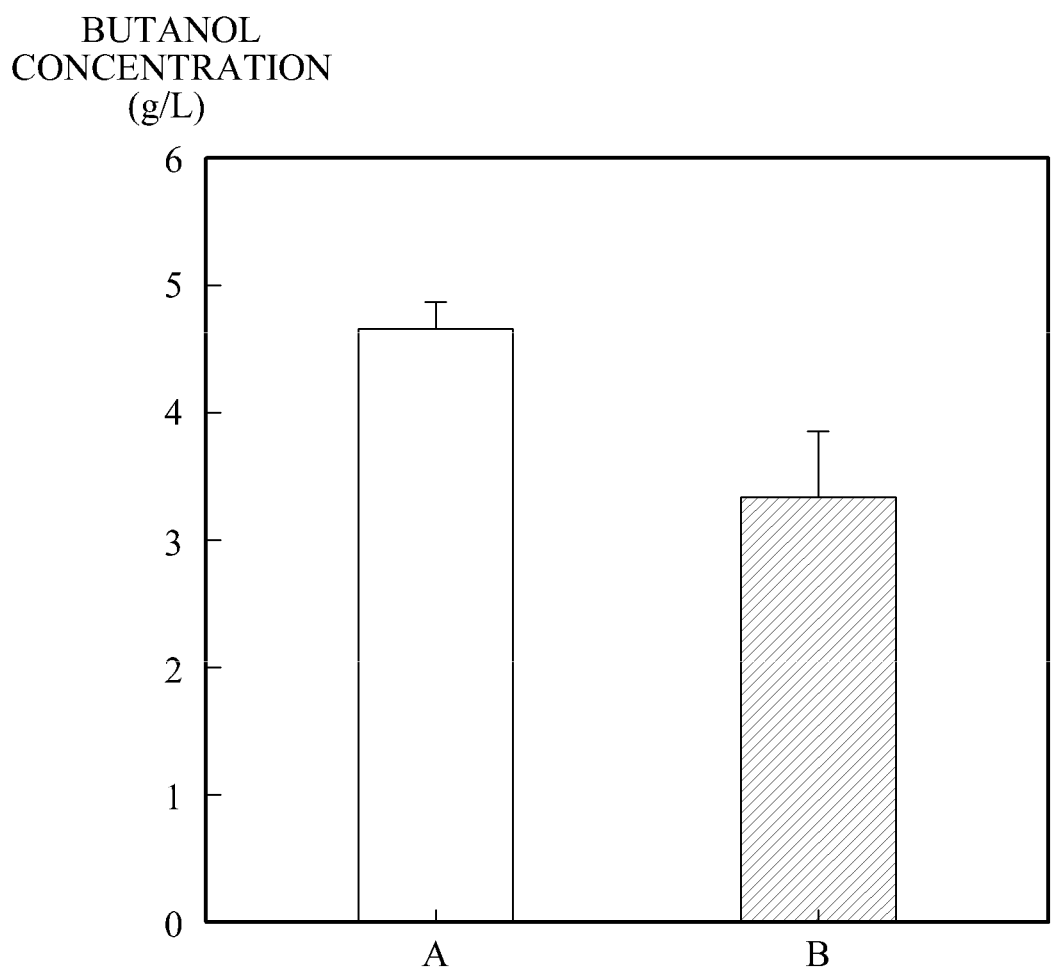
FIG. 12 is a graph illustrating a comparison of concentrations of butanol produced by *Clostridium beijerinckii* ATCC 35702 strain.

FIG. 12 is a graph illustrating a comparison of concentrations of butanol produced by the Clostridium beijerinckii ATCC 35702 strain. Referring to FIG. 12, when the ethanol fermentation waste containing pentose generated in the ethanol production was used as a culture medium (A), the concentration of butanol was 4.7±0.2 g/L, and when the Clostridium culture medium (B) was used, the concentration of butanol was 3.3±0.5 g/L. From this result, it was found that the production of butanol using the culture medium according to the preparing method of the present invention was improved by at least 42% when compared to that of the control conventionally used in the production of butanol.

Production of Butyric Acid Using Fermentation Waste After Ethanol Fermentation

An ethanol fermentation waste was prepared in the foregoing manner and used in the production of butyric acid. The concentrations of xylose and butyric acid were analyzed using HPLC.

In the production of butyric acid, a strain of Clostridium tyrobutyricum ATCC 25755 was used. After 50 ml of the ethanol fermentation waste was put in a 250 ml flask, 2 ml of a liquid culture of Clostridium tyrobutyricum ATCC 25755 strain was implanted. For cultivation, the culture medium was placed in an anaerobic chamber ($N_2$ 90%, $CO_2$ 5%, $H_2$ 5%) at 37° C. for a period of 60 hours.

As a control, a Clostridium culture medium containing, as a carbon source, xylose of the same concentration as the saccharified solution was used. During cultivation, a pH was maintained at 6 or more using 28% ammonia solution.

When the ethanol fermentation waste containing pentose was used as a culture medium and the Clostridium culture medium was used, the Clostridium beijerinckii ATCC 35702 strain completely consumed the 17 g/L of xylose within 80 hours of cultivation.

FIG. 13 is a graph illustrating a comparison of concentrations of butyric acid produced by the Clostridium tyrobutyricum ATCC 25755 strain. Referring to FIG. 13, the concentration of butyric acid produced on the culture medium (A) containing the ethanol fermentation waste containing pentose generated in the ethanol production was 7.3±0.3 g/L, and the concentration of butyric acid produced on the *Clostridium* culture medium (B) was 7.0±0.1 g/L.

From this result, it was found that the production of butyric acid using the culture medium according to an embodiment of the present invention was greater than or equal to that of the control conventionally used in the production of butyric acid.

The invention claimed is:

1. A method for preparing bio-fuels, the method comprising:
   a) preparing an alcohol fermented solution by fermenting hexose from a mixture comprising at least one pentose sugar and at least one hexose sugar;
   b) separating and purifying the alcohol from the fermented solution to produce a fermentation waste comprising the at least one pentose sugar from the mixture;
   c) preparing a culture medium which comprises at least a portion of the fermentation waste;
   d) inoculating a microorganism into the culture medium; and
   e) culturing the microorganism on the culture medium to generate one or more bio-fuels.

2. The method of claim 1, wherein the mixture of pentose and hexose is produced by physically and chemically pre-processing and saccharifying at least one biomass material selected from the group consisting of a lignocellulosic biomass and a cellulosic biomass.

3. The method of claim 1, wherein the at least one hexose sugar is selected from the group consisting of glucose, galactose, mannose and combinations thereof.

4. The method of claim 1, wherein the microorganism is selected from the group consisting of yeast, *Clostridium, Colon bacillus, Bacillus, Anaeromyxobacter, Alcaligenes, Bacteroides, Escherichia, Lactobacillus, Lactococcus, Pichia, Pseudomonas, Ralstonia, Rhodococcus, Saccharomyces, Streptomyces, Thermus thermophilus (Thermus), Thermotoga, Thermoanaerobacter, Klebsiella, Streptomycetaceae, Actinomycetaceae, Colinebacterium, Zymomonas, Actinobacillus, Anaerobiospirillum, Mannheimia* and combinations thereof.

5. The method of claim 1, wherein the microorganism is cultured on the culture medium in an operation selected from the group consisting of batch, fed-batch, continuous operations, and combinations thereof.

6. The method of claim 1, further comprising:
   f) separating and purifying the one or more bio-fuels produced after culturing the microorganism on the culture medium.

7. The method of claim 1, wherein the one or more bio-fuels is selected from the group consisting of a bio-gas, an alcohol, an alkane-based compound, an alkene-based compound and combinations thereof.

8. The method of claim 7, wherein the bio-gas is selected from the group consisting of methane, hydrogen and combinations thereof.

9. The method of claim 7, wherein the alcohol is selected from the group consisting of ethanol, propanol, butanol, pentanol, hexanol and combinations thereof.

10. The method of claim 1, wherein the preparing of culture medium comprises removing solids from the fermentation waste.

11. The method of claim 1, wherein the preparing of culture medium comprises autolysis of the fermentation waste.

12. The method of claim 1, wherein the at least one pentose sugar is selected from the group consisting of xylose, arabinose and combinations thereof.

13. The method of claim 1, wherein the preparing of culture medium comprises adding a component selected from the group consisting of water, a carbon source, nutrient component and combinations thereof.

* * * * *